(12) United States Patent
Stoesz et al.

(10) Patent No.: US 8,124,096 B2
(45) Date of Patent: Feb. 28, 2012

(54) IMMUNE RESPONSE MODIFIER COMPOSITIONS AND METHODS

(75) Inventors: James D. Stoesz, Inver Grove Heights, MN (US); Alexis S. Statham, Woodbury, MN (US); Myhanh T. Truong, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 273 days.

(21) Appl. No.: 12/309,778

(22) PCT Filed: Jul. 13, 2007

(86) PCT No.: PCT/US2007/016001
§ 371 (c)(1),
(2), (4) Date: Nov. 3, 2009

(87) PCT Pub. No.: WO2008/016475
PCT Pub. Date: Feb. 7, 2008

(65) Prior Publication Data
US 2010/0096287 A1    Apr. 22, 2010

Related U.S. Application Data

(60) Provisional application No. 60/820,876, filed on Jul. 31, 2006.

(51) Int. Cl.
*A61K 39/00* (2006.01)
*A61K 45/00* (2006.01)
*A61L 2/00* (2006.01)

(52) U.S. Cl. .............. 424/184.1; 424/278.1; 422/1

(58) Field of Classification Search .............. None
See application file for complete search history.

(56) References Cited

U.S. PATENT DOCUMENTS

| | | |
|---|---|---|
| RE24,906 E | 12/1960 | Ulrich |
| 3,700,674 A | 10/1972 | Diehl et al. |
| 4,013,665 A | 3/1977 | Crenshaw et al. |
| 4,052,393 A | 10/1977 | Treuner |
| 4,191,767 A | 3/1980 | Warner, Jr. et al. |
| 4,197,403 A | 4/1980 | Warner, Jr. et al. |
| 4,411,893 A | 10/1983 | Johnson et al. |
| 4,689,338 A | 8/1987 | Gerster |
| 4,695,465 A | 9/1987 | Kigasawa et al. |
| 4,698,348 A | 10/1987 | Gerster |
| 4,722,941 A | 2/1988 | Eckert et al. |
| 4,746,515 A | 5/1988 | Cheng et al. |
| 4,751,087 A | 6/1988 | Wick |
| 4,863,970 A | 9/1989 | Patel et al. |
| 4,908,389 A | 3/1990 | Mahjour et al. |
| 5,238,944 A | 8/1993 | Wick et al. |
| 5,446,153 A | 8/1995 | Lindstrom et al. |
| 5,939,090 A | 8/1999 | Beaurline et al. |
| 6,039,969 A | 3/2000 | Tomai et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,425,776 B1 | 7/2002 | Fredl et al. |
| 6,706,728 B2 | 3/2004 | Hedenstrom et al. |
| 7,655,672 B2 | 2/2010 | Statham et al. |
| 2003/0026794 A1 | 2/2003 | Fein |
| 2003/0199538 A1 | 10/2003 | Skwierczynski et al. |
| 2004/0180919 A1 | 9/2004 | Miller et al. |
| 2005/0165043 A1 | 7/2005 | Miller et al. |
| 2005/0175630 A1 | 8/2005 | Raz et al. |
| 2005/0201959 A1 | 9/2005 | David |
| 2006/0183767 A1 | 8/2006 | Mandrea |
| 2007/0123558 A1 | 5/2007 | Statham et al. |

FOREIGN PATENT DOCUMENTS

| | | |
|---|---|---|
| EP | 0 107 455 B1 | 7/1986 |
| EP | 0 187 705 A2 | 7/1986 |
| EP | 0 394 026 | 10/1990 |
| EP | 0 582 581 | 2/1994 |
| EP | 1 512 685 | 3/2005 |
| HU | P0002103-AB | 10/2000 |
| PT | 76045-8 | 12/1985 |
| WO | WO-88/09676 | 12/1988 |
| WO | WO-92/15582 | 9/1992 |
| WO | WO-2005/020995 | 3/2005 |
| WO | WO-2006/029223 | 3/2006 |
| WO | WO-2006/074046 | 7/2006 |

OTHER PUBLICATIONS

Sintzel et al (International Journal of Pharmaceutics vol. 175, pp. 165-176, 1998).*
J. L. Chollet, et al. "Development of a Topically Active Imiquimod Formulation", Pharmaceutical Development and Technology, 4(1), 35-43 (1999).
B. Berman, et al., "Novel Dermatologic uses of the Immune Response Modifier Imiquimod 5% Cream", Skin Therapy Letter, vol. 7, No. 9, Nov. 2002. pp. 1-10.
D. Sauder, "Mechanism of Action and Emerging Role of Immune Response Modifier Therapy in Dermatologic Conditions", Journal of Cutaneous Medicine and Surgery, vol. 8, Supplement 3, pp. 3-12 (2005).

(Continued)

*Primary Examiner* — Albert Navarro
(74) *Attorney, Agent, or Firm* — Edwards Wildman Palmer LLP; Peter J. Manso; Kathryn A. Piffat

(57) ABSTRACT

A pharmaceutical composition comprising 1-(2-methylpropyl)-1H-imidazo[4,5-c]quinolin-4-amine that is stable to sterilization and suitable for topical application directly to tissue sites where the dermis has been breached, and has been sterilized, packaged compositions that have been sterilized, and methods of sterilizing these compositions are disclosed.

38 Claims, No Drawings

OTHER PUBLICATIONS

English Translation of Technical Report JC 04-11 for Peruvian Application No. 000992-2007/OIN dated Jul. 31, 2007.
Product Card for ISP Registry No. F-1930/09 (3M Chile S.A.): Aldara Topical Cream 5% (original with English translation), Printed Jul. 2, 2011.
Expert Report About Invention Patent Application Chile No. 2228-07 dated Jul. 31, 2007 (original with English translation).
Abbasi et al., "Base Induced Cyclization of Some Quinolines. Formation of Fused Nitrogen Heterocyclic Ring System" *Monatshette für Chemie* (1980)111:963-969.
Abbasi et al., "Base Induced Cyclization of Some Quinolines. Formation of Fused Nitrogen Hetercyclic Ring System." *Chemical Abstracts* (1961) 94:47216.
Bachman, et al., "Synthesis of Substituted Quinolylamines. Derivatives of 4-Amino-7-Chioroquinoline." *Journal of Organic Chemistry*, 15(1950), pp. 1278-1284.
Backeberg et al., "The Reaction between Hydrazine Hydrate and 4-Chloroquinoline Derivatives." *Journal of Chemistry Society* (1938)pp. 972-977.
Backeberg, O.G. "The Reaction between Phenylhdrazine and 4-Chloroquinoline Derivatives, and the Preparation of the Corresponding 4-Benezeneazo-and 4-Amino-compounds", *Journal of Chemical Society*(1938), pp. 1083-1087.
Baranov et al., "Imidazo[4,5-c]quinolines," *Chemical Abstracts* (1976), 85:94362.
Bartek et al., "Percutaneous Absorption, In Vitro," Animal Models in Dermatology, with Relevance to Human Dermatopharmacology and Dermatotoxicology, *Churchill Livingtone* (New York) (1975), pp. 103-120.
Berènyi et al., "Ring Transformation of Condensed Dihydro-astriazines," *Journal of Heterocyclic Chemistry*, vol. 18 (1981), pp. 1537-1540.
Bhargava, H.N., Ph.D., "The Present Status of Formulation of Cosmetic Emulsions," *Drug Development and Industrial Pharmacy*, 13(13)(1987), pp. 2363-2387.
Billmeyer, Fred W., "Polymer Chains and Their Characterization," *Textbook of Polymer Science* (1971), pp. 84-85.
Chien et al., "Transdermal Controlled Administration of Indomethacin. I. Enhancement of Skin Permeability," *Pharmaceutical Research*, vol. 5:2 (1988), pp. 103-106.
Cohen et al., "Penetration of 5-Fluorouracil in Excised Skin," *The Journal of Investigative Dermatology*, 62:5 (1974) pp. 507-509.
Cooper, Eugene. R., "Increased Skin Permeability for Lipophilic Molecules," *Journal of Pharmaceutical Sciences*, vol. 73, No. 8 (1984), pp. 1153-1156.
Green, et al., "Rapid, Quantitative, Semiautomated Assay for Virus-Induced and Immune Human Interferons," *Journal of Clinical Microbiology*, 12:3 (1980), pp. 433-438.
Jain et al., "Chemical and Pharmacological Investigations of Some w-Substituted Alkylamino-3-aminopyridines," *Journal of Medicinal Chemistry* , (1986) vol. 11: 87-92.
Kern, et al., "Treatment of Experimental Herpesvirus Infections with Phosphonoformate and Some Comparisons with Phosphonoacetate," *Antimocrobial Agents and Chemotherapy*, 14:6 (1978), pp. 817-823.
Koenigs et al., "Uber die Einwirkung von Hydrazin en auf 4-Chiorchinaldin," *Chimische Berichte*, (1947), 80:143-149.
Lachman et al., "The Theory and Practice of Industrial Pharmacy," *The Theory and Practice of Industrial Pharmacy, Lea & Febiger*, Philadelphia, 2nd Edition (1976), pp. 220-229.
Loftsson et al., "The Effect of Vehicle Additives on the Transdermal Delivery of Nitroglycerin," *Pharmaceutical Research*, vol. 4:5 (1987), pp. 436-437.
Overall, Jr., et al., "Activity of Human Recombinant and Lymphoblastoid Interferons in Human and Heterologous Cell Lines," *Journal of Interferon Research* (1984), vol. 4, pp. 529-533.
Stanberry, et al., "Genital Herpes in Guinea Pigs: Pathogenesis of the Primary Infection and Description of Recurrent Disease," *The Journal of Infectious Diseases*, 146:3(1982), pp. 397-404.
Stoughton, Richard B., "Animal Models for In Vitro Percutaneous Absorption," *Animal Models in Dermatology Relevance to Human Dermatopharmacology and Dermatotoxicology* Churchill Livingstone (New York) (1975), pp. 121-132.
Stoughton, Richard B., "Vasoconstrictor Activity and Percutaneous Absorption of Glucocorticosteroids," *Archives of Dermatology*, vol. 99 (1969), pp. 753-756.
Surrey et al., "The Synthesis of Some 3-Nitro- and 3-Amino-4-dialklaminoalkiaminoquinoline Derivatives," *Journal of the American Chemical Society* (Jun. 1951) 73:2413-2416.
Weissberger & Taylor, "Quinolines." *The Chemistry of Heterocyclic Compounds*, (1977) pp. 562-563.
Yu et al., "Percutaneous Absorption of Nicardipine and Ketorolac in Rhesus Monkeys," *Pharmaceutical Research*, vol. 5:7(1998), pp. 457-462.
Hengge et al., "Topical immunomodulators—progress towards treating inflammation, infection, and cancer", *The Lancet Infectious Diseases*, vol. 1, Oct. 2001.
Hengge Errata, *The Lancet Infectious Diseases*, vol. 2, Apr. 2002.
Hansen et al., "Sterilization and Preservation by Radiation Sterilization", *Disinfection, Sterilization, and Preservation*, Fifth Edition, Chapter 37, Seymour S. Block, Ph.D.; Lippincott, Williams & Wilkins, 2001.
ISO11137 (Sterilization and Healthcare Products—Requirements for Validation and Routine Control—Radiation Sterilization), Annex B, 1995.
The Delphion Inegrated View: INPADOC Record Bouman et al., "Preparation and purification of lovastatin derivatives used as hydroxymethyl glutaryl coenzyme A reductase inhibitors-comprises adjusting pH, removing cells used to prepare them, heating and contacting with resin," (http://www.delphion.com/details?pn=HU00002103AB) and Derwent Record (http://www.delphion.com/derwent/p/dwdetails?icnt=HU&patent number=00002103A2&p...) for Hungarian Application HU0002103AB Acession No. 1998-570544/200225 (Feb. 15, 2008) (3 pages).
The Delphion Integrated View: INPADOC Record, Ciba Geigy AG, "Imidazo (4,5-c) quinoline prepn.—consists of reduction of a lower alkylene di:oxy cpd. through reaction with ammonia, etc.), or cpd. of formula (II) is reacted with e.g. ammonia," (http://www.delphion.com/details?pn=PT00076045B) and Derwent Record (http://www.delphion.com/derwent/p/dwdetails?icnt=PT&patent number=00076045A &p...) for Portuguese Patent PT0076045B Accession No. 1984-168891/198427 (Feb. 15, 2008) (3 pages).
Office Action dated Aug. 26, 2011 for corresponding Chile Patent Application No. 2228-07 and English Translation.
Opposition to corresponding Peru Patent Application 00992-2007/OIN from Unimed del Peru (Jan. 7, 2009) and English translation thereof and attachments thereto.
Technical Report JC 04-11/a (Sep. 23, 2011) for corresponding Peru Patent Application 000992-2007/OIN and English Translation thereof.
Resolution No. 000159-2011/CIN-INDECOPI (Oct. 25, 2011) for corresponding Peru Patent Application 000992-2007/OIN and English translation thereof.

* cited by examiner

IMMUNE RESPONSE MODIFIER COMPOSITIONS AND METHODS

CROSS-REFERENCES TO RELATED APPLICATIONS

The present application is a 35 U.S.C. §371 national stage of PCT application PCT/US2007/016001, filed 13 Jul. 2007, which claims priority of U.S. Provisional Application Ser. No. 60/820,876, filed 31 Jul. 2006, the disclosures of all of which are incorporated herein by reference.

FIELD OF THE INVENTION

The present invention relates to pharmaceutical compositions for topical delivery of immune response modifying drugs.

BACKGROUND

There has been a major effort in recent years to discover new drug compounds that act by stimulating certain key aspects of the immune system, as well as by suppressing certain other aspects (see, e.g., U.S. Pat. Nos. 6,039,969 and 6,200,592). These compounds, sometimes referred to as immune response modifiers (IRMs), appear to act through basic immune system mechanisms known as toll-like receptors to induce selected cytokine biosynthesis and may be used to treat a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis), and $TH_2$-mediated diseases (e.g., asthma, allergic rhinitis, atopic dermatitis), and are also useful as vaccine adjuvants. Unlike many conventional anti-viral or anti-tumor compounds, the primary mechanism of action for IRMs is indirect, by stimulating the immune system to recognize and take appropriate action against a pathogen.

Many of the IRM compounds are imidazoquinoline amine derivatives (see, e.g., U.S. Pat. No. 4,689,338), but a number of other compound classes are now known as well (see, e.g., U.S. Pat. Nos. 5,446,153; 6,194,425; and 6,110,929).

Pharmaceutical compositions containing IRM compounds are disclosed in U.S. Pat. Nos. 5,238,944; 5,939,090; and 6,425,776; European Patent 0 394 026; and U.S. Patent Publication 2003/0199538. The IRM compound, 1-(2-methylpropyl)-1H-imidazo[4,5-c]quinolin-4-amine, has been commercialized in a topical formulation, ALDARA, for the treatment of actinic keratosis, basal cell carcinoma, or anogenital warts associated with human papilomavirus.

However, providing therapeutic benefit by topical application of an IRM compound for treatment of a particular condition at a particular location or of a particular tissue can be hindered by a variety of factors, such as, for example, chemical degradation of the IRM compound and/or other ingredients, and physical instability of the composition (e.g., separation of components, thickening, precipitation or agglomerization of active ingredient, and the like).

Therefore, there is a continuing need for new and/or improved IRM formulations.

SUMMARY

It is believed that topically delivered IRM compounds have a number of beneficial uses (such as, e.g., healing diabetic foot ulcers and reducing scars from trauma or surgery), where the composition is applied to open or recently disrupted skin. However, one difficulty in doing so is that for such uses it may be necessary for the composition to be sterile, and sterilization processes can degrade many IRM compounds and/or the compositions containing them.

It has now been found that a topical pharmaceutical composition comprising an immune response modifier drug compound can be made that is stable to sterilization and suitable for topical application.

In one aspect, the present invention provides a topical pharmaceutical composition comprising an immune response modifier drug compound that is stable to sterilization and suitable for topical application directly to tissue sites where the dermis has been breached; wherein the drug compound is 1-(2-methylpropyl)-1H-imidazo[4,5-c]quinolin-4-amine; and wherein the composition has been sterilized. For certain embodiments, the sterilization can be accomplished using electron beam radiation.

In another aspect, the present invention provides a packaged composition that includes a packaging material and the above pharmaceutical composition enclosed within the packaging material wherein the packaged composition has been terminally sterilized.

In another aspect, the present invention provides a method of sterilizing the above pharmaceutical composition or the above packaged composition, comprising the step of irradiating the composition with electron beam radiation at a sterilizing dose sufficient to achieve a sterility assurance level of at least $10^{-3}$.

The term "comprises" and variations thereof do not have a limiting meaning where these terms appear in the description and claims.

As used herein, "a," "an," "the," "at least one," and "one or more" are used interchangeably. Thus, for example, a complex that comprises "a" preservative can be interpreted to mean that the complex includes "one or more" preservatives. Similarly, a composition comprising "a" complex can be interpreted to mean that the composition includes "one or more" complexes.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used individually and in various combinations. In each instance, the recited list serves only as a representative group and should not be interpreted as an exclusive list.

DETAILED DESCRIPTION OF ILLUSTRATIVE EMBODIMENTS OF THE INVENTION

Sterilized topical compositions containing IRMs have not been previously reported. ALDARA cream (available from 3M Company), which contains the IRM, 1-(2-methylpropyl)-1H-imidazo[4,5-c]quinolin-4-amine, has however surprisingly been found to be sterilizable, and much more stable to sterilization than many other IRM compounds.

A preferred method of sterilizing 1-(2-methylpropyl)-1H-imidazo[4,5-c]quinolin-4-amine compositions is using radiation sterilization, such as an electron beam or e-beam radiation. This is surprising in part because irradiation sterilization of drug products is well known to cause degradation, and has prompted the FDA to issue a ruling that all irradiated drug products will be treated as new drug products, requiring submission and approval of a NDA (21 C.F.R. §310.502). However, radiation sterilization using an electron beam has been found to be a preferred method in the case of 1-(2-methylpropyl)-1H-imidazo[4,5-c]quinolin-4-amine formulations. Other approaches to sterilization can also be used, such as gamma radiation. Heat sterilization is less desirable because of possible difficulties with formulation instability.

In one aspect, the present invention is directed to a topical pharmaceutical composition comprising an immune response modifier drug compound that is stable to sterilization and suitable for topical application directly to tissue sites where the dermis has been breached; wherein the drug compound is 1-(2-methylpropyl)-1H-imidazo[4,5-c]quinolin-4-amine; and wherein the composition has been sterilized.

As used herein, a pharmaceutical composition that has been sterilized has a Sterility Assurance Level (SAL) of at least $10^{-3}$. For certain embodiments, the SAL is $10^{-3}$. For certain embodiments the SAL is at least $10^{-6}$. For certain embodiments, the SAL is $10^{-6}$. The SAL is the probability of any given product unit being non-sterile after exposure to a validated sterilization process. For an SAL of at least the probability of any given product unit being non-sterile is one in at least one thousand, for example, one in one thousand, one in ten thousand, one in one hundred thousand, one in one million, and so on. For an SAL of at least $10^{-6}$, the probability of any given product unit being non-sterile is one in at least one million, for example, one in one million, one in ten million, and so on. Conformance to the European Standard EN556, which defines the SAL as $10^{-6}$, can be advantageous. At this SAL, there is one surviving microorganism per one million product units, and the product can be labeled sterile. Methods of verifying the SAL are known. (See ISO11137 (Sterilization of Healthcare Products—Requirements for Validation and Routine Control—Radiation Sterilization 1995 [Annex B])).

For certain embodiments, the pharmaceutical composition has been sterilized by exposure to electron beam radiation. Sterilization of certain materials, including certain health care products, by exposure to electron beam radiation is a known process. (For a discussion of radiation sterilization, including sterilization by exposure to electron beam radiation, see Chapter 37, "Sterilization and Preservation by Radiation Sterilization" in Disinfection, Sterilization and Preservation, 5$^{th}$ Edition, Seymor S. Block, pp. 729-746, Lippincott, Williams and Wilkins, Philadelphia, Pa. (2001).

The sterile pharmaceutical composition is particularly suitable for topical application directly to tissue sites where the dermis has been breached. Such applications are useful, for example, for reversing, preventing, or reducing scarring that can result from certain skin conditions (e.g., acne), infections (e.g., leishmaniasis), and injury (abrasions, punctures, lacerations, or surgical wounds). Suitability for application to such tissue sites includes, for example, a viscosity that permits ease of application, a pH in a range that is sufficiently non-irritating, and the absence of microorganisms which might cause infections.

As used herein, a pharmaceutical composition that is sterilizable is "stable" to sterilization in that it can be stored for an extended period of time and does not significantly change in chemical content or physical properties as a result of the sterilization conditions and the period of storage. This can be measured by evaluating the changes in content of various components of the composition before and after sterilization and over time. For example, for compositions that include methylparaben and/or propylparaben, the content of each of these components does not change by more than JO percent for a composition to be stable. More specifically, for example, as described in the Test Methods herein, preferably, a cream that contains methylparaben and propylparaben in a laminate sachet passes testing if the methylparaben and propylparaben content are within the ranges, inclusive, of 0.18 percent to 0.22 percent and 0.018 percent to 0.022 percent by weight, respectively, after stability testing. Alternatively, stability can be measured by evaluating the formation of impurities, particularly drug-related impurities, over time. In this context, for certain embodiments including any one of the above embodiments, a stable composition contains a total weight of the drug impurities that is not more than 1 percent of the weight of the 1-(2-methylpropyl)-1H-imidazo[4,5-c]quinolin-4-amine. For certain of these embodiments, any single drug impurity is present in an amount not more than 0.3 percent of the weight of the 1-(2-methylpropyl)-1H-imidazo[4,5-c]quinolin-4-amine. For certain of these embodiments, total weight of the drug impurities is not more than 0.5 percent of the weight of the 1-(2-methylpropyl)-1H-imidazo[4,5-c]quinolin-4-amine. For certain of these embodiments, total weight of the drug impurities is not more than 0.3 percent of the weight of the 1-(2-methylpropyl)-1H-imidazo[4,5-c]quinolin-4-amine. For certain of these embodiments, any single drug impurity is present in an amount not more than 0.1 percent of the weight of the 1-(2-methylpropyl)-1H-imidazo[4,5-c]quinolin-4-amine.

Preferably, the pharmaceutical composition that has been sterilized is an emulsion (more preferably, an oil-in-water emulsion) that is typically in the form of a cream, although other forms, such as ointments, lotions or gels, can be advantageously sterilized and used for topical applications. As stated above, the sterile pharmaceutical composition contains 1-(2-methylpropyl)-1H-imidazo[4,5-c]quinolin-4-amine. For certain embodiments, including any one of the above embodiments, the composition includes one or more fatty acids, such as isostearic acid.

For certain embodiments, including any one of the above embodiments of the pharmaceutical composition that has been sterilized, the composition further comprises a preservative. For certain of these embodiments, the preservative is selected from the group consisting of methylparaben, propylparaben, benzyl alcohol, and mixtures thereof. Such components are found to be stable after the pharmaceutical composition is sterilized and during a period of storage. Other optional additives may also be included.

1-(2-Methylpropyl)-1H-imidazo[4,5-c]quinolin-4-amine is in a class of compounds known as immune response modifiers (IRMs) that are known antiviral agents that can induce interferon biosynthesis. Such compounds can be used to treat viral infections, such as Type I or Type II Herpes simplex infections and genital warts, as well as numerous other diseases, such as rheumatoid arthritis, warts, eczema, hepatitis B, psoriasis, multiple sclerosis, essential thrombocythaemia, and cancer, such as basal cell carcinoma and other neoplastic diseases. Such compounds can also be used to improve skin quality, including treating or preventing scarring resulting from a surgical wound, for example, as described in U.S. Publication Nos. 2004/0180919 A1 and 2005/0165043 A1. The amount of 1-(2-methylpropyl)-1H-imidazo[4,5-c]quinolin-4-amine present in a composition of the invention will be an amount effective to treat, prevent the recurrence of, or promote immunity to the targeted disease state, or to improve skin quality.

For certain embodiments, including any one of the above embodiments, the total amount of 1-(2-methylpropyl)-1H-imidazo[4,5-c]quinolin-4-amine is at least 0.5 percent by weight, based on the total weight of the composition. For certain of these embodiments, the total amount of 1-(2-methylpropyl)-1H-imidazo[4,5-c]quinolin-4-amine is at least 1 percent by weight, based on the total weight of the composition. For certain of these embodiments, the total amount of 1-(2-methylpropyl)-1H-imidazo[4,5-c]quinolin-4-amine is at least 4.5 percent by weight, based on the total weight of the composition.

For certain embodiments, the total amount of 1-(2-methylpropyl)-1H-imidazo[4,5-c]quinolin-4-amine is no more than 9 percent by weight, based on the total weight of the composition. For certain of these embodiments, the total amount of 1-(2-methylpropyl)-1H-imidazo[4,5-c]quinolin-4-amine is no more than 5.5 percent by weight, based on the total weight of the composition.

A cream preferably includes 1-(2-methylpropyl)-1H-imidazo[4,5-c]quinolin-4-amine in an amount of it least 0.5 percent, preferably at least 1 percent, and more preferably at least 4.5 percent, based on the total weight of the cream. A cream preferably includes 1-(2-methylpropyl)-1H-imidazo[4,5-c]quinolin-4-amine in an amount of no greater than 9 percent, and more preferably no greater than 5.5 percent, based on the total weight of the cream.

An ointment preferably includes 1-(2-methylpropyl)-1H-imidazo[4,5-c]quinolin-4amine in an amount of least 0.5 percent, preferably at least 1 percent, and more preferably at least 4.5 percent, based on the total weight of the ointment. The total amount of 1-(2-methylpropyl)-1H-imidazo[4,5-c]quinolin-4-amine in an ointment is preferably no greater than 9 percent, and more preferably no greater than 5.5 percent, based on the total weight of the ointment.

The total amount of one or more fatty acids present in a composition will generally be in an amount sufficient to solubilize the 1-(2-methylpropyl)-1H-imidazo[4,5-c]quinolin-4-amine compound. The total amount of one or more fatty acids present in a composition may, for example, be at least 5 percent by weight, at least 15 percent by weight, or at least 20 percent by weight, based on the total weight of the composition. For compositions having 5% 1-(2-methylpropyl)-1H-imidazo[4,5-c]quinolin-4-amine, the total amount of fatty acid, preferably isostearic acid, in the composition will generally be at least 15% by weight, and more preferably at least 20% by weight, for example about 25% by weight, based on the total weight of the composition. The total amount of one or more fatty acids present in a composition is no more than 45 percent by weight or no more than 30 percent by weight, based on the total weight of the composition. Preferably, the total amount of one or more fatty acids present in a composition is about 25 percent by weight based on the total weight of the composition.

Typical fatty acids for use in compositions described herein include isostearic acid, oleic acid, myristic acid, palmitic acid, palmitoleic acid, margaric acid, stearic acid, linoleic acid, linolenic acid, or mixtures thereof. Preferred fatty acids include isostearic acid, oleic acid, or mixtures thereof. A preferred fatty acid is isostearic acid.

Optionally, a cream can contain emollients, emulsifiers, and/or thickeners. Emollients, such as long chain alcohols, e.g., cetyl alcohol, stearyl alcohol, and cetearyl alcohol; hydrocarbons such as petrolatum and light mineral oil; or acetylated lanolin can be included in creams described herein. A cream can contain one or more of these emollients. A cream preferably includes a total amount of emollient of at least 5 percent, based on the total weight of the cream. A cream preferably includes a total amount of emollient of no greater than 30 percent, and more preferably no greater than 10 percent, based on the total weight of the cream.

Emulsifiers such as nonionic surface active agents, e.g., polysorbate 60 (available from ICI Americas), sorbitan monostearate, polyglyceryl-4 olcate, and polyoxyethylene(4) lauryl ether, can be included in creams described herein. A cream can contain one or more emulsifiers. A cream preferably includes a total amount of emulsifier of at least 2 percent, based on the total weight of the cream. A cream preferably includes a total amount of emulsifier of no greater than 14 percent, and more preferably no greater than 6 percent, based on the total weight of the cream.

Pharmaceutically acceptable thickeners, such as xanthan gum, VEEGUM K (available from R.T. Vanderbilt Company, Inc.), and long chain alcohols (e.g., cetyl alcohol, stearyl alcohol, or cetearyl alcohol) can be used. A cream can contain one or more thickeners. A cream preferably includes a total amount of thickener of at least 3 percent, based on the total weight of the cream. A cream preferably includes a total amount of thickener of no greater than 12 percent, based on the total weight of the cream.

Optionally, one or more additional solubilizing agents such as benzyl alcohol, lactic acid, acetic acid, stearic acid, or hydrochloric acid can be included in the creams described herein. If one or more additional solubilizing agents are used, the total amount present is preferably at least 1 percent, based on the total weight of the cream. If one or more additional solubilizing agents are used, the total amount present is preferably no greater than 12 percent, based on the total weight of the cream.

Optionally, the creams described herein can contain a humectant, such as glycerin, and additional solubilizing agents.

It is known to those skilled in the art that a single ingredient can perform more than one function in a cream, i.e., cetyl alcohol can serve both as an emollient and as a thickener.

Generally, a cream consists of an oil phase and a water phase mixed together to form an emulsion. Preferably, the amount of water present in a cream of the invention is at least 45 percent, based on the total weight of the cream. Preferably, the amount of water present in a cream of the invention is no greater than 85 percent, based on the total weight of the cream.

The oil phase of a cream of the invention can be prepared, for example, by first combining 1-(2-methylpropyl)-1H-imidazo[4,5-c]quinolin-4-amine and one or more fatty acids (if the cream contains benzyl alcohol it can also be added at this point) and beating with occasional stirring to a temperature of 50° C. to 85° C. When the 1-(2-methylpropyl)-1H-imidazo[4,5-c]quinolin-4-amine appears to be completely dissolved, the remaining oil phase ingredients are added and heating is continued until dissolution appears to be complete. The water phase can be prepared by combining all other ingredients and heating with stiffing until dissolution appears to be complete. The creams of the invention are generally prepared by adding the water phase to the oil phase with both phases at a temperature of 65° C. to 75° C. The resulting emulsion is mixed with a suitable mixer apparatus to give the desired cream.

For certain embodiments, including any one of the above embodiments, the pharmaceutical composition is a cream, comprising an oil phase and a water phase in admixture, the composition comprising about 4.5 to about 5.5 percent 1-(2-methylpropyl)-1H-imidazo[4,5-c]quinolin-4-amine, about 20 to about 30 percent isostearic acid, about 1.0 percent to about 2.1 percent benzyl alcohol, about 0.5 percent to about 2.5 percent cetyl alcohol, about 1 percent to about 3.5 percent stearyl alcohol, about 2 percent to about 4 percent petrolatum, about 3 percent to about 4 percent polysorbate 60, about 0.4 percent to about 0.8 percent of sorbitan monostearate, about 1 percent to about 3 percent of glycerin, about 0.18 to about 0.22 percent methylparaben, about 0.018 percent to about 0.022 percent propylparaben, about 0.0 to about 1.0 percent xanthan gum, and about 50 to about 55 percent purified water; all percentages being based upon the total weight of the composition.

For certain embodiments, including any one of the above embodiments, the pharmaceutical composition is a cream, comprising an oil phase and a water phase in admixture, the oil phase comprising about 4.5 to about 5.5 percent 1-(2-methylpropyl)-1H-imidazo[4,5-c]quinolin-4-amine, about 20 to about 30 percent isostearic acid, about 1.0 percent to about 2.1 percent benzyl alcohol, about 0.5 percent to about 2.5 percent cetyl alcohol, about 1 percent to about 3.5 percent stearyl alcohol, about 2 percent to about 4 percent petrolatum, about 3 percent to about 4 percent polysorbate 60, and about 0.4 percent to about 0.8 percent of sorbitan monostearate, and the water phase comprising about 1 percent to about 3 percent of glycerin, about 0.18 to about 0.22 percent methylparaben, about 0.018 percent to about 0.022 percent propylparaben, about 0.0 to about 1.0 percent xanthan gum, and about 50 to about 55 percent purified water; all percentages being based upon the total weight of the composition.

As indicated above, the pharmaceutical composition that has been sterilized should have a viscosity that permits ease of application, which includes the ability to readily apply the desired amount to the tissue site without causing further trauma. Accordingly, for certain embodiments, including any one of the above embodiments of the pharmaceutical composition that has been sterilized, the viscosity is at least 2,000 cps and not more than 35,000 cps.

The composition should also maintain a pH in a range that is sufficiently non-irritating, since a pH that is too low or too high could cause tissue damage. Accordingly, for certain embodiments, including any one of the above embodiments of the pharmaceutical composition that has been sterilized, the pH is stable. That is, the pH is maintained within an established range after the composition has been sterilized and during a period of storage. For certain embodiments, including any one of the above embodiments, the pH is not less than 4 and not more than 5.5.

An ointment preferably contains an ointment base in addition to 1-(2-methylpropyl)-1H-imidazo[4,5-c]quinolin-4-amine and one or more fatty acids. A pharmaceutically acceptable ointment base such as petrolatum or polyethylene glycol 400 (available from Union Carbide) in combination with polyethylene glycol 3350 (available from Union Carbide) can be used. The amount of ointment base present in an ointment of the invention is preferably at least 60 percent, based on the total weight of the ointment. The amount of ointment base present in an ointment of the invention is preferably no greater than 95 percent, based on the total weight of the ointment.

In one embodiment, the ointment base is comprised of white petrolatum. For certain of these embodiments, the ointment base is further comprised of mineral oil and/or white wax. For certain of these embodiments, the ointment base further comprises stearyl alcohol and/or cetyl alcohol.

In another embodiment, the ointment base is comprised of mineral oil. For certain of these embodiments, the ointment base further comprises white wax and/or cetyl esters wax. For certain of these embodiments, the ointment base further comprises water.

In another embodiment, the ointment base is comprised of white petrolatum and stearyl alcohol and/or cetyl alcohol. For certain of these embodiments, the ointment base further comprises water. For certain of these embodiments, the ointment base further comprises propylene glycol.

In another embodiments, the ointment base is comprised of one or more poly(ethylene glycol) polymers. For certain of these embodiments, the poly(ethylene glycol) polymers are poly(ethylene glycol) (Ave. $M_n$=400) and poly(ethylene glycol) (Ave. $M_n$=3350). The term "Ave. $M_n$" refers to the number average molecular weight.

Optionally, an ointment can also contain emollients, emulsifiers, and/or thickeners. The emollients, emulsifiers, and/or thickeners and the preferred amounts thereof described above in connection with creams are also generally suitable for use in an ointment of the invention.

An ointment can be prepared, for example, by combining 1-(2-methylpropyl)-1H-imidazo[4,5-c]quinolin-4-amine with one or more fatty acids and heating with occasional stirring to a temperature of 65° C. When the 1-(2-methylpropyl)-1H-imidazo[4,5-c]quinolin-4-amine appears to be completely dissolved, the remaining ingredients are added and heated to 65° C. The resulting mixture is mixed with a suitable mixer while being allowed to cool to room temperature.

For certain embodiments, the pharmaceutical composition is an ointment, comprising about 1 to about 5.5 percent 1-(2-methylpropyl)-1H-imidazo[4,5-c]quinolin-4-amine, about 5 to about 30 percent isostearic acid, about 8 percent to about 13 percent mineral oil, about 44 percent to about 66 percent white petrolatum, about 2 percent to about 4 percent cetyl alcohol, about 0.5 percent to about 1 percent lanolin, such as, for example, acetylated lanolin, about 2 percent to about 3 percent polyglycerol oleate (commercially available from Akzo Nobel Surfactants under the trade designation WITCONOL 14), and about 5 to about 8 percent aluminum stearate; all percentages being based upon the total weight of the composition.

For certain embodiments, the pharmaceutical composition is an ointment, comprising about 1 to about 5.5 percent 1-(2-methylpropyl)-1H-imidazo[4,5-c]quinolin-4-amine, about 6 to about 30 percent isostearic acid, about 38 percent to about 56 percent poly(ethylene glycol) (Ave $M_n$=400), about 22 percent to about 33 percent poly(ethylene glycol) (Ave $M_n$=3350), and about 3 percent to about 5 percent stearyl alcohol; all percentages being based upon the total weight of the composition.

In another aspect, the present invention provides a packaged composition that includes a packaging material and any one of the above pharmaceutical composition embodiments enclosed within the packaging material wherein the packaged composition has been terminally sterilized. As used herein, "terminally sterilized" means that the packaged composition has been sterilized after the pharmaceutical composition is enclosed or sealed within the packaging material.

For certain embodiments, including any one of the above embodiments of the packaged composition, the packaging material is a multi-layer laminate. Such multi-layer laminates comprise two or more layers with one or more of the layers being a moisture barrier. For certain of these embodiments, the multi-layer laminate comprises a contact layer, an outer layer, and a moisture barrier layer disposed between the contact layer and outer layer. In the packaged composition, the contact layer comes in contact with the pharmaceutical composition. One or more tie layers can be disposed between the layers for bonding the layers together. The tie layers can be adhesives or extruded polymeric materials. For example, the outer layer and the moisture barrier layer can be bonded together with an extruded polymer (e.g., polyethylene).

Examples of materials that can be incorporated into adhesives suitable for use in the multi-layer laminate, particularly for bonding the contact layer to the moisture barrier layer and/or the outer layer to the moisture barrier layer, include (ethylene acrylic acid) ethylene ethylacrylate (EEA), ethylene methylacrylate (EMA), ethylene vinyl acetate (EVA), ethylene methyl acrylic acid (EMAA), and a urethane.

An example of a material for a tie layer that is suitable, particularly for bonding the outer layer to the moisture barrier layer, is an extruded low-density polyethylene.

The thickness of each layer and that of the overall laminate construction is sufficient to provide the desired moisture barrier properties and mechanical strength. Each layer and the overall laminate are also sufficiently thin to be readily torn by hand.

The outer layer is sufficiently thick to provide mechanical strength. The outer layer is preferably at least 5 microns (μ) thick. The outer layer is preferably no greater than 50 microns thick, or, in some embodiments, no greater than 20 microns thick.

The outer layer may include an organic polymer, such as polyethylene terephthalate (PET), paper, cellophane, or other clear protective packaging layer, for example. For certain embodiments, the outer layer includes PET, which is about 0.48 mil (12 microns) thick.

For certain embodiments, including any one of the above embodiments of the packaged composition, the moisture barrier layer comprises a metal foil. A metal foil such as aluminum or copper is suitable. For certain embodiments, the metal foil is at least 5 microns thick. For certain embodiments, the thickness of the metal foil is no greater than 50 microns. For certain embodiments, the thickness of the metal foil is about 9 microns. For certain embodiments, the metal foil moisture barrier is a layer that includes aluminum foil, which is preferably about 9 microns thick.

The contact layer is preferably at least about 25 microns thick. The contact layer is preferably no greater than about 80 microns thick.

Examples of materials for the contact layer include acrylonitrile-methyl acrylate (AMA) copolymer, polyethylene (PE), PET, or combinations thereof. In one embodiment, the contact layer is acrylonitrile-methyl acrylate copolymer. In one embodiment, the polymeric contact layer is about 51 microns (2 mils) thick.

An example of a suitable laminate is Product No. 60012-36 available from Ludlow Coated Products (Constantine, Mich.) that includes a 12 micron thick PET outer layer, a layer of white low-density polyethylene (number 10) tie layer, a 9 micron thick aluminum layer, an adhesive, and a BAREX acrylonitrile-methyl acrylate copolymer layer.

For certain embodiments, including any one of the above embodiments of the packaged composition, the packaging material is in the form of a single-use sachet. A single-use sachet is a small packet capable of containing sufficient pharmaceutical composition for one topical application, for example, about 250 mg.

In one embodiment, the packaged composition is ALDARA cream in a single-use sachet. ALDARA cream in a single-use sachet is available from 3M (St. Paul, Minn.). ALDARA cream is a topical pharmaceutical composition containing 1-(2-methylpropyl)-1H-imidazo[4,5-c]quinolin-4-amine and isostearic acid in an oil-in-water emulsion.

For certain alternative embodiments of the packaged composition that includes a packaging material and any one of the above pharmaceutical composition embodiments, the packaging material is a tube. For certain of these embodiments, the tube is single-use. Alternatively, for certain of these embodiments, the tube is multi-use. A tube that is single-use is sized to contain sufficient pharmaceutical composition for one topical application, for example, about 250 mg. A tube that is multi-use is sized to contain sufficient pharmaceutical composition for two or more topical applications.

For certain of the above embodiments where the packaging material is a tube, the tube is an aluminum tube. For certain of these embodiments, the aluminum tube has an epoxy phenolic lacquer liner. The epoxy phenolic lacquer liner is on the inside of the tube and contacts the pharmaceutical composition.

Alternatively, for certain of the above embodiments where the packaging material is a tube, the tube is comprised of a multi-layer laminate, the multi-layer laminate comprising a contact layer, an outer layer, and a moisture barrier layer disposed between the contact layer and outer layer.

The multi-layer laminate can be sealed to form a package, such as a sachet or tube, under appropriate sealing conditions sufficient to provide a good seal and not damage the package contents. Such conditions can be determined readily by one of skill in the art. A typical sealing temperature for laminates is at least 150° C., and preferably at least 200° C. Preferably the sealing temperature is no greater than 350° C.

In another aspect, the present invention provides a method of sterilizing the pharmaceutical composition, including any one of the above pharmaceutical composition embodiments, or the packaged composition, including any one of the above packaged composition embodiments, comprising the step of irradiating the composition or packaged composition with electron beam radiation at a sterilizing dose sufficient to achieve a sterility assurance level of at least $10^{-3}$. For certain of these embodiments, the sterility assurance level is at least $10^{-6}$. For certain of these embodiments, the sterility assurance level is $10^{-6}$. Sterilizing dose refers to the amount of energy deposited in the composition or packaged composition. This is commonly referred to as the absorbed dose in gray (Gy) units, where 1 Gy is equivalent to absorption of 1 joule/kg, and 1 kilogray (kGy) is equivalent to the absorption of $10^3$ joule/kg. For certain embodiments, the sterilizing dose is at least 10 kGy. For certain embodiments, the sterilizing dose is at least 25 kGy.

The composition or packaged composition can be irradiated using a electron beam irradiator. A horizontal scan, vertical scan, or other available scan configuration can be used. The composition held in a suitable container or the packaged composition can be conveyed through the electron beam with the beam directed downward or upward into the composition or packaged composition (horizontal scan). In another example, the composition held in a suitable container or the packaged composition can be conveyed in a carrier through the electron beam with the beam directed horizontally into the composition or packaged composition (vertical scan). With any chosen configuration, the electron beam and the composition or packaged composition are oriented with respect to each other such that the entire composition is irradiated. If desired, more than one pass through the electron beam can be made.

The energy of the electrons in the electron beam can be, for example, at least 1 million electron volt (MeV), at least 5 MeV, or at least 10 MeV. For certain embodiments, a 10 MeV electron beam is used.

EXAMPLES 1-(2-Methylpropyl)-1H-imidazo[4,5-c]quinolin-4-amine-containing cream is available from 3M (St. Paul, Minn.) under the trade designation ALDARA (imiquimod 5% cream). ALDARA cream is manufactured by a typical oil-in-water cream non-sterile process. The two phases are prepared separately, and the oil phase is added to the aqueous phase under vacuum. The emulsion is homogenized and mixed until the temperature has reached 35° C., and then the emulsion is cooled to 30° C. with continuous mixing. The ALDARA cream used in the present investigation was manufactured as a 100 kilogram batch and stored below 25° C. until sachet filling. The cream was then packaged into 250 milligram (mg) sachets for commercial use at 3M Health Care Ltd., Loughborough, England and was shipped to 3M Northridge, Calif. Sachets (12,096) were then shipped to 3M St. Paul, Minn. for testing. The samples were stored at ambient temperature for six months prior to sterilization.

An e-beam radiation sterilization system using a 10 MeV horizontal beam with a roller conveyor system at Titan Scan Technology (Denver, Colo.) was used to irradiate 4,020 sachets of the ALDARA cream. The sachets were irradiated by passing the sachets through the electron beam unit twice with an actual dose of 25.7-27.8 kilo Gray (kGy). Control samples and e-beam irradiated samples were stored at 25° C. and 60% relative humidity and evaluated for stability at 3 months, 6 months, 12 months, 18 months, and 24 months. Stability was evaluated by testing appearance, pH, viscosity, level of impurities, level of 1-(2-methylpropyl)-1H-imidazo[4,5-c]quinolin-4-amine (imiquimod), and level of preservatives (i.e., methylparaben, propylparaben) according to the test methods described below. The results are presented in Tables 1 through 5 below.

Test Methods:
Appearance

The appearance of the cream from three sachets was visually inspected for color with the aide of a color chart (#0=white, #1=off white, #2=slightly buff color, #332 buff color, #4=slightly yellow color). The cream was visually inspected for uniform appearance.

pH

The pH was measured with an Orion 616500 electrode calibrated with pH 4 and 7 buffers. The electrode was inserted directly into a sample of the cream and allowed to stabilize. The pHs for two samples were recorded for each time point, and the average is reported below.

Viscosity

The viscosity of the cream, measured at 20° C.±0.5° C., was determined using either a Haake RS100, RS150 or RS600 rheometer by running a stress ramp test (shear stress range from 0.1 to 125 Pa, over 150 seconds) and calculating the viscosity at a defined shear rate of 4.4 sec−1. Three samples were tested at each time point, and the average is reported below.

1-(2-Methylpropyl)-1H-imidazo[4,5-c]quinolin-4-amine Content, Methylparaben Content, and Propylparaben Content An external standard, reverse-phase, ion-paired, isocratic high performance liquid chromatography (HPLC) method was used to determine the 1-(2-methylpropyl)-1H-imidazo[4,5-c]quinolin-4-amine content and levels of preservatives (e.g., methylparaben, propylparaben) in control and irradiated cream formulations.

The liquid chromatograph is equipped with a 258 nut detector and an octylsilane (C8), 4.6 mm×15 cm column that contains 5 μm packing. The chromatographic column is run at room temperature. The mobile phase is a filtered and degassed mixture of 28% acetonitrile and 72% aqueous solution containing 0.2% octyl sodium sulfate and 1% triethylamine adjusted to pH 2.0 with 85% phosphoric acid ($H_3PO_4$). The flow rate is 2.0 mL per minute.

The sample is made by accurately weighing approximately 300 mg of ALDARA cream into a 100 mL volumetric flask and bringing the flask to volume with a 25:74:1 mixture of acetonitrile:water:hydrochloric acid. The flask is shaken and sonicated for five minutes to extract and dissolve the components of interest.

A standard solution is prepared by accurately weighing reference standards of 1-(2-methylpropyl)-1H-imidazo[4,5-c]quinolin-4-amine and the preservatives into a volumetric flask and diluting to volume with a 25:74:1 mixture of acetonitrile:water:hydrochloric acid. Serial dilutions of the standard solution are made to achieve the desired concentration. Separate 20 microliter injections are made of filtered sample and standard solutions. The analyte concentrations are calculated from the respective peak areas and are reported as weight percents (% w/w) based on the weight of the initial sample.

Impurity Content

An external standard, reverse-phase, gradient HPLC method was used to determine the levels of identified and unidentified impurities in the control and irradiated creams. The liquid chromatograph is equipped with a 308 nm detector and an octylsilane (C8), 4.6 mm×15 cm column that contains 5 μm packing. The chromatographic column is run at room temperature. The mobile phase is a filtered and degassed mixture of acetonitrile and aqueous ammonium phosphate buffer solution containing 0.51% phosphoric acid, and adjusted to pH 2.5 with concentrated ammonium hydroxide. The mobile phase gradient starts at 10% acetonitrile, with zero initial hold time, and then increases linearly to 70% acetonitrile after 15 minutes, with zero final hold time. The column is then re-equilibrated to 10% acetonitrile. The flow rate is 2.0 mL per minute.

The sample is made by accurately weighing approximately 300 mg of ALDARA cream into a 100 mL volumetric flask and bringing the flask to volume with a 25:74:1 mixture of acetonitrile:water:hydrochloric acid. The flask is sonicated to extract and dissolve the component of interest.

A standard solution is prepared by accurately weighing reference standard of each identified impurity into a volumetric flask and diluting to volume with a 25:74:1 mixture of acetonitrile:water:hydrochloric acid. Serial dilutions of the standard solution are made to achieve a concentration equivalent to 0.1% of the concentration of imiquimod in the sample solution. Separate 200 microliter injections are made of filtered sample and standard solutions. The impurity concentrations are calculated from the respective peak areas and are reported as weight percents (% w/w) based on the weight of 1-(2-methylpropyl)-1H-imidazo[4,5-c]quinolin-4-amine.

TABLE 1

Appearance

| Treatment | | Time Point (Months) | | | | | |
|---|---|---|---|---|---|---|---|
| | | Initial | 3 | 6 | 12 | 18 | 24 |
| control | Color Scale | 1 | 1 | 0 | 1 | 2 | 3 |
| | Cream Appears Uniform | YES | YES | YES | YES | YES | YES |
| e-beam | Color Scale | 1 | 3 | 3 | 3 | 3 | 4 |
| | Cream Appears Uniform | YES | YES | YES | YES | YES | YES |

TABLE 2

| | pH | | | | | |
|---|---|---|---|---|---|---|
| Treatment | Initial | 3 M | 6 M | 12 M | 18 M | 24 M |
| control | 5.3 | 5.0 | 4.9 | 5.0 | 4.8 | 4.8 |
| e-beam | 5.2 | 4.8 | 4.8 | 4.7 | 4.7 | 4.6 |

TABLE 3

| | Viscosity [(centipoises (cps)] | | | | | |
|---|---|---|---|---|---|---|
| Treatment | Initial | 3 M | 6 M | 12 M | 18 M | 24 M |
| control | 11017 | 9474 | 8369 | 6765 | 5313 | 3889 |
| e-beam | 10827 | 8589 | 9210 | 5335 | 3861 | 2571 |

TABLE 4

| | Sum of Impurity Contents Above or At 0.01% (% w/w) | | | | | |
|---|---|---|---|---|---|---|
| Treatment | Initial | 3 M | 6 M | 12 M | 18 M | 24 M |
| control | 0.02 | 0.19 | 0.02 | 0.01 | 0.01 | 0.01 |
| e-beam | 0.06 | 0.21 | 0.09 | 0.09 | 0.10 | 0.16 |

There was no significant difference between the control and irradiated samples when tested for uniform appearance and pH. The color of the irradiated cream changed after three months storage and remained the same color through 18 months storage before turning slightly yellow al 24 months. The color of the control cream changed after 18 months storage.

Irradiation had no effect on initial viscosity of the active cream. The control and irradiated active creams had similar viscosity up to six months. At the 12, 18, and 24 month time points the viscosity of the irradiated cream dropped more than the control, but was still well above the lower specification for ALDARA cream, 2000 cps.

The content of imiquimod, methylparaben, and propylparaben was measured in the control and irradiated creams at 3, 6, 9, 12, 18, and 24 months. There was no significant change over time in the levels for any of these components for either the control or the irradiated creams. The content of imiquimod, methylparaben, and propylparaben in the control and irradiated creams after 24 months of storage at 25° C. and 60% relative humidity is shown in Table 5.

TABLE 5

| Imiquimod, Methylparaben, and Propylparaben Content (% w/w) at 24 months | | | |
|---|---|---|---|
| Test | Control | Irradiated | Specification |
| Imiquimod Content | 5.09 | 5.01 | 4.50-5.50 |
| Methylparaben Content | 0.20 | 0.19 | 0.18-0.22 |
| Propylparaben Content | 0.020 | 0.019 | 0.018-0.022 |

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What we claim is:

1. A topical pharmaceutical composition comprising an immune response modifier drug compound that is stable to sterilization and suitable for topical application directly to tissue sites where the dermis has been breached;
    wherein the drug compound is 1-(2-methylpropyl)-1H-imidazo[4,5-c]quinolin-4-amine; and
    wherein the composition has been sterilized.

2. The pharmaceutical composition of claim 1, wherein the composition has been sterilized by exposure to electron beam radiation.

3. The pharmaceutical composition of claim 1, wherein any single drug impurity is present in an amount not more than 0.3 percent of the weight of the 1-(2-methylpropyl)-1H-imidazo[4,5-c]quinolin-4-amine, and the total weight of the drug impurities is not more than 1 percent of the weight of the 1-(2-methylpropyl)-1H-imidazo[4,5-c]quinolin-4-amine.

4. The pharmaceutical composition of claim 3, wherein the total weight of the drug impurities is not more than 0.5 percent of the weight of the 1-(2-methylpropyl)-1H -imidazo[4,5-c]quinolin-4-amine.

5. The pharmaceutical composition of claim 4, wherein the total weight of the drug impurities is not more than 0.3 percent of the weight of the 1-(2-methylpropyl)-1H -imidazo[4,5-c]quinolin-4-amine.

6. The pharmaceutical composition of claim 3, wherein any single drug impurity is present in an amount not more than 0.1 percent of the weight of the 1-(2-rnethylpropyl)-1H-imidazo[4,5-c]quinolin-4-amine.

7. The pharmaceutical composition of claim 1, wherein the total amount of 1-(2-methylpropyl)-1H-imidazo[4,5-c]quinolin-4-amine is at least 0.5 percent by weight, based on the total weight of the composition.

8. The pharmaceutical composition of claim 7 wherein the total amount of 1-(2-methylpropyl)-1H-imidazo[4,5-c]quinolin-4-amine is at least 1 percent by weight, based on the total weight of the composition.

9. The pharmaceutical composition of claim 7 wherein the total amount of 1-(2-methylpropyl)-1H-imidazo[4,5-c]quinolin-4-amine is at least 4.5 percent by weight, based on the total weight of the composition.

10. The pharmaceutical composition of claim 1, wherein the total amount of 1-(2-methylpropyl)-1H-imidazo[4,5-c]quinolin-4-amine is no more than 9 percent by weight, based on the total weight of the composition.

11. The pharmaceutical composition of claim 10 wherein the total amount of 1-(2-methylpropyl)-1H-imidazo[4,5-c]quinolin-4-amine is no more than 5.5 percent by weight, based on the total weight of the composition.

12. The pharmaceutical composition of claim 1, wherein the composition further comprises a preservative.

13. The pharmaceutical composition of claim 12 wherein the preservative is selected from the group consisting of methylparaben, propylparaben, benzyl alcohol, and mixtures thereof.

14. The pharmaceutical composition of claim 1, wherein the composition is a cream, comprising an oil phase and a water phase in admixture, the composition comprising about 4.5 to about 5.5 percent 1-(2-methylpropyl)-1H-imidazo[4,5-c]quinolin-4-amine, about 20 to about 30 percent isostearic acid, about 1.0 percent to about 2.1 percent benzyl alcohol, about 0.5 percent to about 2.5 percent actyl alcohol, about 1 percent to about 3.5 percent stearyl alcohol, about 2 percent to about 4 percent petrolatum, about 3 percent to about 4 percent polysorbate 60, about 0.4 percent to about 0.8 percent of sorbitan monostearate, about 1 percent to about 3 percent of glycerin, about 0.18 to about 0.22 percent methylparaben, about 0.018 percent to about 0.022 percent propylparaben, about 0.0 to about 1.0 percent xanthan gum and about 50 to about 55 percent purified water; all percentages being based upon the total weight of the composition.

15. The pharmaceutical composition of claim 1, wherein the viscosity is at least 2,000 cps and not more than 35,000 cps.

16. The pharmaceutical composition of claim 1, wherein the pH is stable.

17. The pharmaceutical composition of claim 1, wherein the pH is not less than 4 and not more than 5.5.

18. A packaged composition that includes a packaging material and the pharmaceutical composition of claim 1, enclosed within the packaging material wherein the packaged composition has been terminally sterilized.

19. The packaged composition of claim 18, wherein the packaging material is a multi-layer laminate.

20. The packaged composition of claim 19, wherein the multi-layer laminate comprises a contact layer; an outer layer; and a moisture barrier layer disposed between the contact layer and outer layer.

21. The packaged composition of claim 20, wherein the moisture barrier layer comprises a metal foil.

22. The packaged composition of claim 20, wherein the contact layer comprises an acrylonitrile-methyl acrylate copolymer.

23. The packaged composition of claim 18, wherein the packaging material is in the form of a single-use sachet.

24. The packaged composition of claim 18, wherein the packaged composition is a 5% imiquimod cream in a single-use sachet.

25. The packaged composition of claim 18, wherein the packaging material is a tube.

26. The packaged composition of claim 25, wherein the tube is single-use.

27. The packaged composition of claim 25, wherein the tube is multi-use.

28. The packaged composition of any one of claims 25, 26, and 27, wherein the tube is an aluminum tube.

29. The packaged composition of claim 28, wherein the aluminum tube has an epoxy phenolic lacquer liner.

30. The packaged composition of any one of claims 25, 26, and 27, wherein the tube is comprised of a multi-layer laminate, the multi-layer laminate comprising a contact layer, an outer layer, and a moisture barrier layer disposed between the contact layer and outer layer.

31. A method of sterilizing the pharmaceutical composition of claim 1, comprising the step of irradiating the composition with electron beam radiation at a sterilizing dose sufficient to achieve a sterility assurance level of at least $10^{-3}$.

32. The method of claim 31, wherein the sterility assurance level is $10^{-6}$.

33. The method of claim 31 or claim 32, wherein the sterilizing dose is at least 10 kGy.

34. The method of claim 31 or claim 32, wherein the sterilizing dose is at least 25 kGy.

35. A method of sterilizing the packaged composition of claim 18, comprising the step of irradiating the composition with electron beam radiation at a sterilizing dose sufficient to achieve a sterility assurance level of at least $10^{-3}$.

36. The method of claim 35, wherein the sterility assurance level is $10^{-6}$.

37. The method of claim 35 or claim 36, wherein the sterilizing dose is at least 10 kGy.

38. The method of claim 35 or claim 36, wherein the sterilizing dose is at least 25 kGy.

* * * * *